(12) United States Patent
Delgado et al.

(10) Patent No.: US 7,295,651 B2
(45) Date of Patent: Nov. 13, 2007

(54) STATIONARY COMPUTED TOMOGRAPHY SYSTEM AND METHOD

(75) Inventors: Eladio Clemente Delgado, Burnt Hills, NY (US); Zhiyuan Ren, Malta, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 11/172,716

(22) Filed: Jun. 30, 2005

(65) Prior Publication Data

US 2007/0003004 A1  Jan. 4, 2007

(51) Int. Cl.
*H05G 1/70* (2006.01)
*H05G 1/00* (2006.01)

(52) U.S. Cl. .......................... 378/92; 378/10

(58) Field of Classification Search ............. 378/9–10, 378/19, 91, 92, 96, 101, 114–116, 210, 901
See application file for complete search history.

(56) References Cited

U.S. PATENT DOCUMENTS 5,305,363 A * 4/1994 Burke et al. .................... 378/4
6,275,559 B1 * 8/2001 Ramani et al. ................. 378/4
6,489,742 B2 * 12/2002 Lumsden ..................... 318/727
6,901,131 B2  5/2005 Edic et al. ..................... 378/19
2005/0100127 A1 * 5/2005 Zhao et al. .................... 378/19
2005/0111610 A1 * 5/2005 De Man et al. ............... 378/10
2005/0190878 A1 * 9/2005 De Man et al. ................ 378/9
2005/0226363 A1 * 10/2005 Edic et al. ...................... 378/9

* cited by examiner

*Primary Examiner*—Courtney Thomas
*Assistant Examiner*—Anastasia S. Midkiff
(74) *Attorney, Agent, or Firm*—Fletcher Yoder

(57) ABSTRACT

A radiographic imaging system is presented. The system includes a system controller and a plurality of sub-system controllers. Each sub-system controller is configured to facilitate generation of a radiation beam through an imaging volume in a desired sequence. In addition, the system includes a first communication link configured to couple the system controller and each of the sub-system controllers, where the first communication link is configured to communicate sequencing commands and imaging protocol data. The system also includes a second communication link configured to couple the system controller and each of the sub-system controllers, where the second communication link is configured to communicate X-ray source event data. The X-ray source event data comprises a plurality of pulses of individually addressable radiation sources. Additionally, the system includes one or more detector sections configured to receive a transmitted radiation beam.

36 Claims, 5 Drawing Sheets

STATIONARY COMPUTED TOMOGRAPHY SYSTEM AND METHOD

BACKGROUND

The invention relates generally to the field of computed tomography (CT) imaging systems, and more particularly to geometries and interconnection configurations for the stationary CT systems in which a single detector or multiple detectors and distributed radiation source elements are fixedly positioned in an imaging system scanner.

Many applications exist for computed tomography imaging systems. Developed over recent decades, such imaging systems provide a powerful tool for imaging internal features of subjects of interest, typically presented as slices and volumes. In general, the systems consist of a source that directs X-ray radiation through the subject of interest onto a detector. As will be appreciated, the source of radiation may be any type of radiation that is able to penetrate the subject of interest. The X-ray source and detector, in traditional systems, are mounted on a rotational gantry and spun at a relatively high rotational rate (e.g., two revolutions per second), although faster and slower speeds are also used. Measurements of the incident X-ray intensity on the detectors are acquired at many locations during rotation and are stored for later analysis and processing. The systems then compute useful reconstructed images by processing the acquired intensity measurements, allowing determination of the location of features of interest within the subject, and reconstruction of useful images.

Typically, current techniques employ an X-ray tube and detector electronics rotating in a large gantry. However, they are limited by the need to rotate the source and detector elements about the subject to obtain a 360-degree scan. Increasing interest exists for CT systems that will not require such rotation, and that may be called "stationary CT systems." As will be appreciated, a stationary CT system may be composed of a large number of X-ray sources, such as field emitters, which need to be properly sequenced and precisely timed. Also, the precise on and off timing is typically in the microsecond range. Consequently, interfaces using properly balanced transmission lines need to be implemented in order to accomplish such narrow sequencing and synchronizing pulses. In addition, a large volume of wires is required to interconnect a system controller to the X-ray source drive circuits and the other functional blocks of the stationary CT system. The performance of these systems is disadvantageously sensitive to the lengths of the interconnecting wires. In addition, single ended, high impedance digital interconnections employed by these systems are highly susceptible to common mode noise.

There is a need, therefore, for a robust, high noise-immunity system wiring interconnection scheme that is less sensitive to interconnection lengths. In particular, there is a significant need for a design that can lighten interconnections between the system components and enhance communication between sub-functions of the system by reducing control wiring and enhancing timing and synchronization. There is a particular need for systems that can generate high-quality images while reducing the mechanical and electrical problems associated with interconnecting and controlling the plurality of X-ray sources in a full arc of the stationary system.

BRIEF DESCRIPTION

Briefly, in accordance with aspects of the present technique, a radiographic imaging system is presented. The system includes a system controller and a plurality of sub-system controllers. Each sub-system controller is configured to facilitate generation of a radiation beam through an imaging volume in a desired sequence. In addition, the system includes a first communication link configured to couple the system controller and each of the sub-system controllers, where the first communication link is configured to communicate sequencing commands and imaging protocol data. The system also includes a second communication link configured to couple the system controller and each of the sub-system controllers, where the second communication link is configured to communicate X-ray source event data. The X-ray source event data comprises a plurality of pulses of individually addressable radiation sources. Additionally, the system includes one or more detector sections configured to receive a transmitted radiation beam.

In accordance with other aspects of the present technique, the system includes one or more data acquisition modules. Additionally, the system includes a third communication link configured to couple the system controller and the one or more data acquisition module. The third communication link communicates X-ray source event data to the one or more data acquisition modules, and reads out imaging data from the one or more data acquisition modules. Further, the system also includes a fourth communication link configured to couple all the sub-system controllers and data acquisition modules for synchronizing the X-ray sources and detectors.

Methods designed to implement communications of the type mentioned above are also provided.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
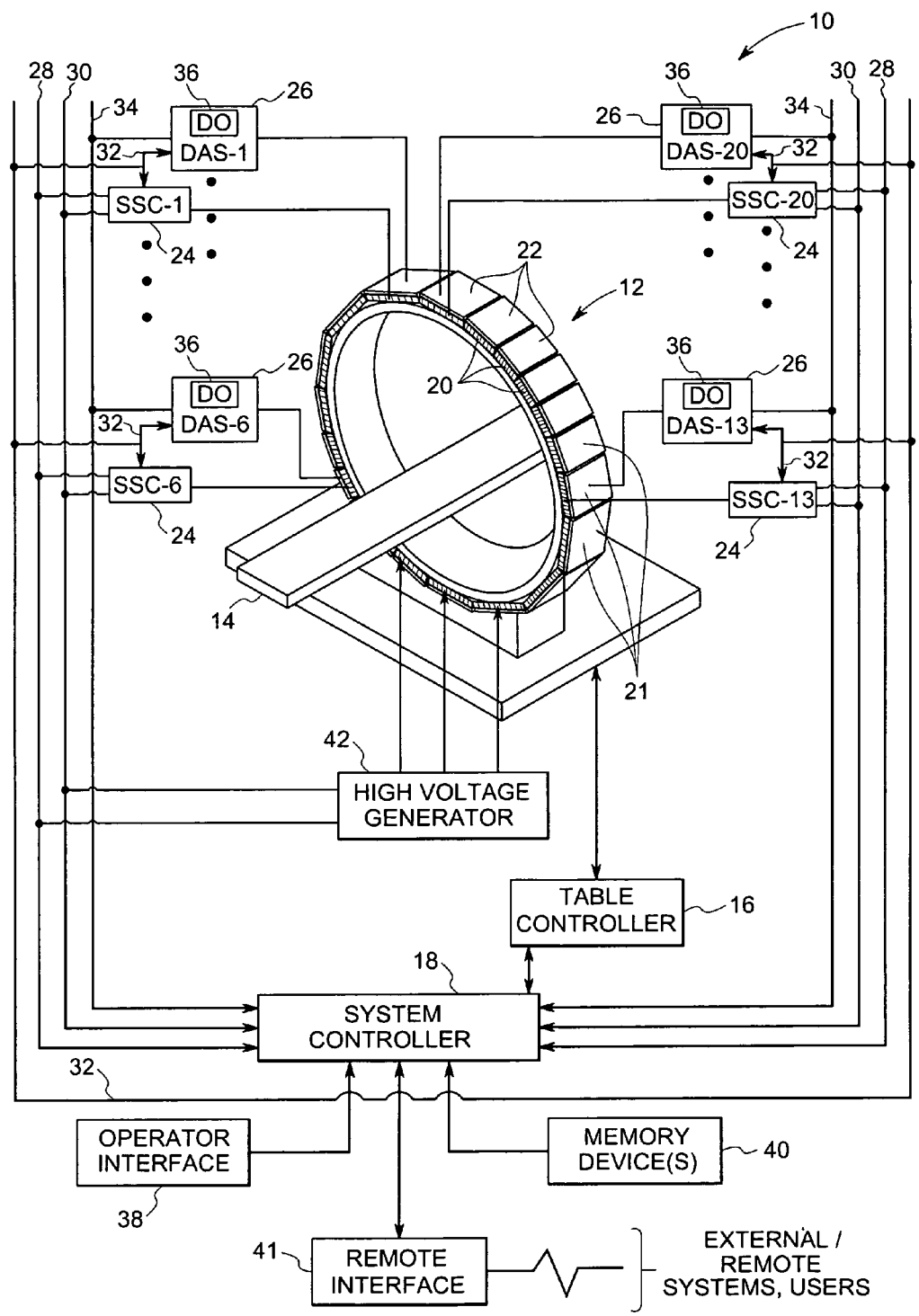
FIG. 1 is a diagrammatical representation of an exemplary stationary CT system, according to aspects of the present technique.

Turning now to FIG. 1, an exemplary stationary computed tomography (CT) system 10, in accordance with aspects of the present technique, is illustrated. As will be appreciated by those skilled in the art, the figures are for illustrative purposes and are not drawn to scale. The CT system 10 comprises a scanner 12 and may be configured to receive a table 14 or other support for a patient (not shown), or, more generally, an object (not shown) to be scanned. The table 14 may be moved through an aperture in the scanner 12 to appropriately position the object in an imaging volume or plane scanned during imaging sequences. The system 10 further includes a table controller 16 which may function under the direction of a system controller 18.

Further, the scanner 12 may be formed of a support structure and one or more stationary and distributed sources 20 of X-ray radiation and one or more stationary digital detectors 22. In accordance with an exemplary embodiment of the present technique, the stationary sources 20 and the stationary detectors 22 may be arranged in an array around the arc of the stationary CT system 10. The stationary CT system 10 includes a large number of X-ray sources 20 and detectors 22 that are interconnected, properly sequenced and precisely timed. An exemplary strategy to interconnect and control the X-ray sources 20 and detectors 22 is presented. In one embodiment, the stationary CT system 10 may be partitioned into a plurality of sub-systems, where each of the plurality of sub-systems is configured to function independently while working in synchronization with the other sub-systems or functions.

By way of example, the full arc of the stationary CT system 10 may include a large number (e.g., on the order of four thousand) of X-ray sources 20 that need to properly sequenced and precisely timed. The X-ray sources 20 disposed around the arc of the stationary CT system 10 may be divided into a plurality of sub-systems 21. In a presently contemplated configuration, four thousand X-ray sources 20 may be divided into twenty sub-systems 21. Accordingly, each of the twenty sub-systems 21 may include two hundred X-ray sources 20. In the embodiment illustrated of FIG. 1, the system 10 is shown as having twenty segments of detectors 22. However, it should be noted that the one or more detectors 22 may be disposed in a contiguous array around the scanner 12. Alternatively, the one or more detectors 22 may be distributed in a plurality of detector segments, where the number of detector segments is greater than or less than the number of sub-systems 21.

In addition, each of the plurality of sub-systems 21 may be coupled to a respective sub-system controller 24. Each of the sub-system controllers 24 may include a gate drive circuit which will be described in greater detail with reference to FIGS. 2-4.

Each of the sub-system controllers 24 may be configured to facilitate generation of a radiation beam through the object or patient in a desired sequence. In other words, each of the sub-system controllers 24 may be configured to regulate timing for discharges of X-ray radiation from each of the X-ray sources 20, which is directed from points around the scanner 12 toward a detector segment 22 that is disposed on a side of the system opposite from the X-ray source 20. Accordingly, each sub-system controller 24 may be configured to trigger one or more independently addressable X-ray sources within the respective sub-system 21 at each instant in time for creating multiple data acquisitions or frames of imaging data.

In certain arrangements, for example, a sub-system controller 24 may be configured to trigger emission of radiation in sequences so as to collect adjacent or non-adjacent acquisitions of transmitted X-ray intensity around the scanner 12. That is, imaging sequences may call for sub-systems around the CT imaging volume to be triggered for data acquisition in an order following their physical order, or in any other desired sequence. Many such measurements may be collected in an examination sequence. Further, each of the detector segments 22 typically including a number of detector elements, may be coupled to a respective data acquisition module or data acquisition system 26. The data acquisition system 26 is configured to receive signals from the detector segment 22 and process the signals for storage and later image acquisition reconstruction. Also, each of the plurality of data acquisition systems 26 may include a respective data out module 36. The data out module 36 may be configured to facilitate reading out the acquired data to read out electronics (not shown). Table controller 16, then, serves to appropriately position the table 14 and the object in a plane in which the radiation is emitted, or, in the present context, generally within a volume to be imaged. The table 14 may be displaced between imaging sequences or during certain imaging sequences, depending upon the imaging protocol employed.

In a presently contemplated configuration, each of the plurality of sub-system controllers 24 is coupled to the system controller 18 via a first communication link 28. This first communication link may be any suitable network link, such as a control area network (CAN) bus. The first communication link 28 may be configured to communicate large volumes of data in real-time. Alternatively, the first communication link 28 may be configured to defer the communication of data to a later time. In addition, each of the plurality of sub-system controllers 24 may be coupled to the system controller 18 via a second communication link 30, such as a RS485 bus. The second communication link 30 may be configured to communicate X-ray source event data in real-time. Further, each of the plurality of data acquisition systems 26 may be coupled to the system controller 18 via a third communication link 34. The third communication link 34 may be configured to communicate X-ray source event data to the data acquisition system 26. Further, the third communication link 34 may be configured to facilitate reading out imaging data from the data acquisition system 26. In one embodiment, the third communication link 34 may include an Ethernet connection or a fiber optical link. However, other forms of communication links may also be employed as the third communication link 34. Also, in a presently contemplated configuration, all the sub-system controllers 24 may be coupled to all the data acquisitions system 26 via a fourth communication link 32. The fourth communication link 32 may be configured to communicate X-ray source event data to synchronize the X-ray sources 20 and detectors 22. In one embodiment, the fourth communication link 32 may include a RS485 bus line.

The system controller 18 generally regulates the operation of the plurality of sub-system controllers 24, the table controller 18, the plurality of data acquisition systems 26 and a high voltage generator 42. The system controller 18 may thus cause each sub-system controller 24 to trigger emission of X-ray radiation, and coordinate such emissions during imaging sequences defined by the system controller 18. The system controller 18 may also regulate movement of the table 14 in coordination with such emission so as to collect transmitted X-ray intensity measurement data of volumes of particular interest, or in various modes of imaging, such as helical modes. The system controller 18 also receives data acquired by data acquisition system 26 and coordinates storage and processing of the data.

It should be borne in mind that the controllers, and indeed various circuitry described herein, may be defined by various hardware circuitry, firmware and software. The particular protocols for imaging sequences, for example, will generally be defined by code executed by the system controller 18. Moreover, initial processing, conditioning, filtering, and other operations required on the transmitted X-ray intensity data acquired by the scanner 12 may be performed in one or more of the components depicted in FIG. 1. For example, the detector elements produce analog signals representative of depletion of a charge in photodiodes positioned at locations corresponding to pixels of the acquisition detector 22. Such analog signals may be converted to digital signals by electronics within the scanner 12, and may be transmitted to data acquisition system 26. Partial processing may occur at this point, and the signals are ultimately transmitted to the system controller 18 for further filtering and processing.

With continuing reference to FIG. 1, the system controller 18 is also coupled to an operator interface 38 and to one or more memory devices 40. The operator interface 38 may be integral with the system controller 18, and may generally include an operator workstation for initiating imaging sequences, controlling such sequences, and manipulating data acquired during imaging sequences. The memory devices 40 may be local to the imaging system, or may be partially or completely remote from the system. Thus, imaging devices may include local, magnetic or optical memory, or local or remote repositories for imaged data for reconstruction. Moreover, the memory devices 40 may be configured to receive raw, partially processed or fully processed data for reconstruction. Further, the system controller 18 may also be coupled to a remote interface 41. A remote interface 41 may be included in the system 10 for transmitting data from the imaging system to such remote processing stations or memory devices.

Additionally, the system 10 may include a high voltage generator 42. As will be appreciated, the high voltage generator 42 is an essential component of an X-ray generation system. Typically, X-ray systems require very high voltages commonly in a range from about 5 kilovolts (kV) to about 400 kV. The high voltage generator 42 may be configured to apply a high positive charge to an anode (not shown) of each of the X-ray sources 20. This high positive charge enables acceleration of electrons impinging on the anode. In other words, the high positive charge possesses a strong attractive force to the negative charge of the electrons emitted from the cathode (not shown). Further, the high voltage generator 42 may be coupled to the first and second communication links 28, 30.

As previously noted, the scanner 12 of stationary CT system 10 may include one or more distributed X-ray sources 20 as well as one or more digital detectors 22 for receiving radiation and processing corresponding signals to produce data. The distributed X-ray source 20 may include a series of electron beam emitters (not shown) that are coupled to sub-system controller 24 shown in FIG. 1, and are triggered by the sub-system controller 24 during operation of the scanner 12. The electron beam emitters may be positioned adjacent to a target (not shown). Upon triggering by the sub-system controller 24, the electron beam emitters may emit electron beams (not shown) toward the target. The target, which may, for example, be a tungsten rail or element, emits X-ray radiation, upon impact of the electron beams. The X-ray source 20 may be operated in either reflection or transmission mode. In the reflection mode, X-rays are meant to be produced primarily on the same side of the target as where the electrons impact. In transmission mode, X-rays are produced at the opposite side of the target. The X-ray beams may then be directed toward a collimator (not shown), which is generally opaque to the X-ray radiation, but which includes apertures (not shown). The apertures may be fixed in dimension, or may be adjustable. Also, the apertures permit a portion of the X-ray beams to penetrate through the collimator to form collimated beams that will be directed to the imaging volume of the scanner 12, through the object of interest, and that will impact detector elements on an opposite side of the scanner 12.

A number of alternative configurations for emitters or distributed sources may, of course, be envisaged. Moreover, the individual X-ray sources in the distributed source may emit various types and shapes of X-ray beams. These may include, for example, fan-shaped beams, cone-shaped beams, and beams of various cross-sectional geometries. Similarly, the various components comprising the distributed X-ray source may also vary. In one embodiment, for example, a cold cathode emitter is envisaged which may be housed in a vacuum housing. A stationary anode is then placed in the housing and spaced apart from the emitter. This type of arrangement generally corresponds to the diagrammatical illustration of FIG. 2. Other materials, configurations, and principles of operations may, of course, be employed for the distributed X-ray source. The emission devices may be one of many available electron emission devices, for example, thermionic emitters, carbon-based emitters, photo emitters, ferroelectric emitters, laser diodes, monolithic semiconductors, and so forth.

A plurality of detector elements (not shown) forms one or more detectors 22 that receive the radiation emitted by the distributed X-ray sources 20. Each detector 22 may include detector elements with varying resolution to satisfy a particular imaging application. The detector arrangement may be generally similar to detectors used in conventional rotational CT systems, but is extended around a greater portion or the entire inner surface of the scanner 12. In general, however, the detector 22 includes a series of detector elements and associated signal processing circuitry (not shown). Each detector element may include an array of photodiodes and associated thin film transistors. X-ray radiation impacting the detectors 22 is converted to lower energy photons by a scintillator and these photons impact the photodiodes. A charge maintained across the photodiodes is thus depleted, and the transistors may be controlled to recharge the photodiodes and thus measure the depletion of the charge. By sequentially measuring the charge depletion in the various photodiodes, each of which corresponds to a pixel in the collected data for each acquisition, data is collected that encodes transmitted radiation at each of the pixel locations. This data is processed by the signal processing circuitry, which will generally convert the analog depletion signals to digital values, perform any necessary filtering, and transmit the acquired data to processing circuitry of the imaging system as described above. Although the detector 22 has been described in terms of a scintillator-based energy-integrating device, direct conversion, photon counting, or energy discriminating detectors are equally suitable.

Figure 2:
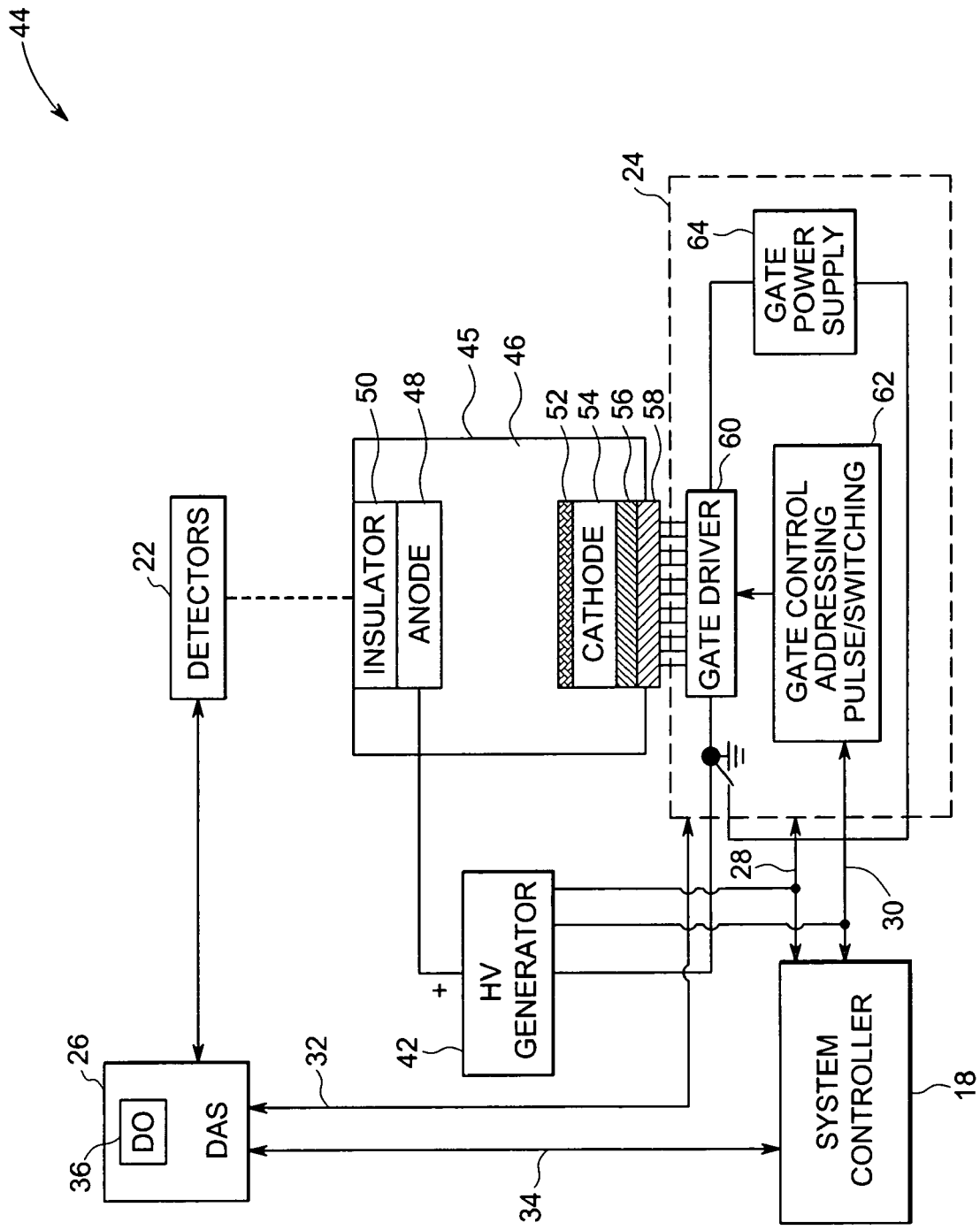
FIG. 2 is a further diagrammatical representation of the stationary CT system of FIG. 1.

FIG. 2 is a diagrammatical view of a physical implementation 44 of the exemplary stationary CT system 10 of FIG. 1. The illustrated embodiment 44 depicts functional blocks of the stationary CT system 10. In a presently contemplated configuration, each of the sub-system controllers 24 is coupled to the system controller 18 via the first communication link 28. As previously noted, the first communication link 28 may be a CAN bus. In addition, each of the plurality of sub-system controllers 24 is coupled to the system controller 18 via the second communication link 30. In one embodiment, the second communication link 30 may be a RS485 bus, as previously noted. Also, the high voltage generator 42 is coupled to the CAN bus 28 and the RS485 bus 30. Also, each of the plurality of data acquisition systems 26 associated with a respective detector segment 22 is coupled to the system controller 18 via the third communication link 34. As previously noted, the data out module 36 is configured to facilitate reading out the acquired data to read out electronics. Further, each of the plurality of sub-system controllers 24 is coupled to a respective data acquisition system 26 via a fourth communication link 32. In one embodiment, the fourth communication link 32 may be another RS485 bus.

With continuing reference to FIG. 2, a portion of an exemplary distributed X-ray source 20 of the type that may be employed in the stationary CT system 10 is illustrated. As shown in FIG. 2, in an exemplary implementation, the distributed X-ray source 20 includes a series of independent addressable emission devices 45 housed in a vacuum housing 46 that are coupled to sub-system controller 24 shown in FIG. 1, and are triggered by the sub-system controller 24 to emit electron beams during operation of the imaging system 10. As previously described, the addressable emission devices 45 are positioned adjacent to a target and, upon triggering by the sub-system controller 24, may emit electron beams toward the target or anode 48. In addition, an insulator 50 may be disposed adjacent to the anode 48.

Also, as illustrated in FIG. 2, the emission device 45 may include an emitter 52, a cathode 54, an emitter mounting 56 and emitter feedthrough 58. Further, in accordance with exemplary aspects of the present technique, for this type of X-ray source, the sub-system controller 24 includes a gate drive module 60. The gate drive module 60 may be driven by a gate control addressing pulse/switching module 62, where the gate control addressing pulse/switching module 62 is configured to facilitate energizing a respective independent addressable source 45. Further, the sub-system controller 24 also includes a gate power supply 64 configured to provide voltage to the gate driver module 60. Additionally, the interconnection scheme 44 of the stationary CT system 10 may also include a high voltage generator 42. As previously noted, the high voltage generator 42 is configured to provide a high voltage to each of the independent addressable sources 45. In particular, the high voltage generator 42 is configured to apply a high positive charge to an anode of each of the X-ray sources 20 (see FIG. 1) thereby facilitating acceleration of electrons impinging on the anode. It may be noted that, in accordance with exemplary aspects of the present technique, balanced and properly terminated high frequency differential transceivers may be employed to communicate between the functional blocks of the stationary CT system 10.

Figure 3:
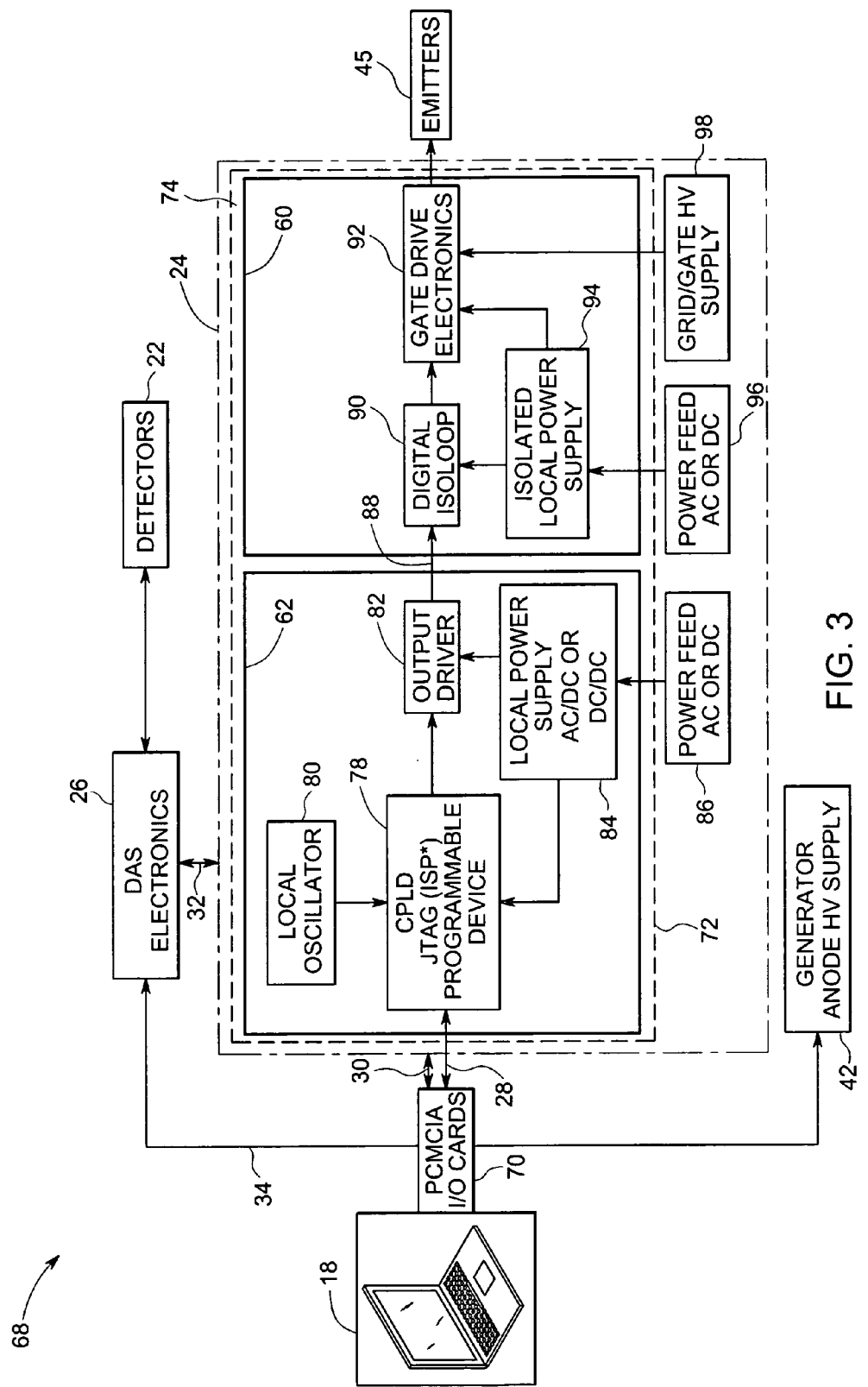
FIG. 3 is diagrammatical representation of emitter electronics for the stationary CT system illustrated in FIG. 2.

Turning now to FIG. 3, a diagrammatical illustration 68 of the emitter electronics that may be configured to control sequencing of the independent addressable X-ray sources is depicted. A system controller 18 is implemented as the heart of the stationary CT system. This system controller 18 is the human interface of the system, and where the system functionality is configured to obtain specific X-ray views.

The system controller 18 is configured to communicate with the emitter electronics via one or more PCMCIA input/output cards 70, for instance. As previously noted, an industrial high noise immunity CAN bus 28 may be configured to facilitate coupling the system controller 18 and the plurality of sub-system controllers 24. Consequently, in a presently contemplated configuration, the CAN bus 28 may be distributed to as many as twenty sub-system controllers 24, where each of the sub-system controllers 24 is configured to control the gates of associated independent addressable sources. It may be noted that each of the plurality of sub-system controllers 24 may communicate a signal indicative of a faulty state to the system controller 18 via the first communication link 28. Also, as previously noted, the high voltage generator 42 may be coupled to the system controller 18 via the CAN bus 28.

Further, the system controller 18 may be configured to communicate with the gate control addressing pulse/switching module 62 of the sub-system controller 24. In one embodiment, the gate control addressing pulse/switching module 62 includes a programmable device 78. A local oscillator 80 may be coupled to the programmable device 78. The programmable device 78 may also be connected to an output driver 82. A local power supply 84 is configured to provide voltage to the programmable device 78 and the output driver 82. In addition, a power feed 86 is coupled to the local power supply 84 and is configured to provide input power to the local power supply 84.

The gate control addressing pulse/switching module 62 is in turn configured to drive the gate drive module 60. This coupling is achieved by connecting the output driver 82 of the gate control addressing pulse/switching module 62 to a digital isoloop 90 of the gate drive module 60 as represented by directional arrow 88, which in turn is coupled to the gate drive electronics 92. The gate drive electronics 92 drives the emitters 45 (see FIG. 2). An isolated local power supply 94 may be configured to provide voltage to the digital isoloop 90, which in turn is fed by a power feed 96. The isolated local power supply 94 is also configured to drive the gate drive electronics 92. In addition, a grid/gate high voltage supply 98 is configured to provide voltage to the gate drive electronics 92. Also, the gate control addressing pulse/switching module 62 and the gate drive module 60 may be enclosed within a lead enclosure 72 in a vacuum chamber 74. The lead enclosure 72 is configured to protect the electronics of the gate control addressing pulse/switching module 62 and the gate drive module 60 from X-ray emission. Further, it may be desirable to ensure that electronics associated with the gate control addressing pulse/switching module 62 and the gate drive module 60 are hermetically sealed and installed to facilitate reduction in the number of feedthroughs through the vacuum chamber 74.

Figure 4:
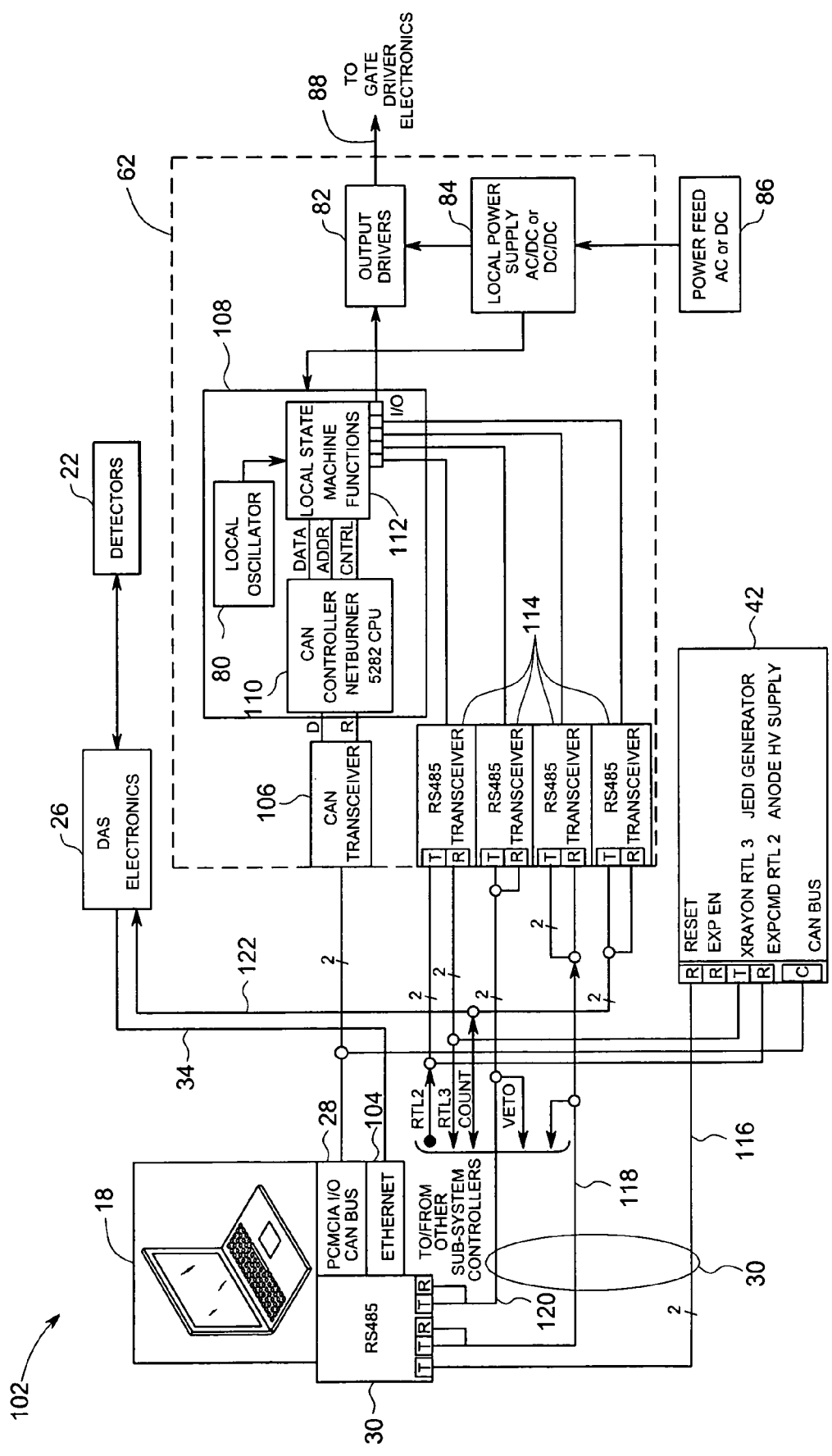
FIG. 4 is diagrammatical representation of emitter driver control electronics for the stationary CT system illustrated in FIG. 2.

FIG. 4 illustrates, in greater detail, a system 102 having the gate control addressing pulse/switching module 62, the desired interfaces and wiring interconnections. In the illustrated embodiment, the system controller 18 is illustrated as communicating with the gate control addressing pulse/switching module 62 via the first communication link 28 and the second communication link 30. The third communication link 34 may include an Ethernet connection 104 to facilitate communication between the system controller 18 and the data acquisition system electronics 26. Alternatively, the third communication link 34 may include any other communication links such as a fiber optical link.

Further, the system controller 18 is coupled to the gate control addressing pulse/switching module 62 via the first communication link 28. The gate control addressing pulse/switching module 62 may include a CAN transceiver 106. The CAN transceiver 106 is configured to communicate with a module 108. The module 108 may include a CAN controller 110, the local oscillator 80 and a local state machine 112. The local state machine 112 may be a fast running state machine configured to precisely produce gate drive pulses commanded by the system controller 18.

With continuing reference to FIG. 4, the system controller 18 is coupled to the gate control addressing pulse/switching module 62 via the second communication link 30. The gate control addressing pulse/switching module 62 may also include a plurality of RS485 transceivers 114. The high voltage supply 42 may be initialized by via the first communication link 28, then synchronized by a pair of RS485 bus lines, such as RTL2 and RTL3. Another RS485 line 116 controls the reset function to the high voltage generator 42. Further, a Start/Controller Counts command may be communicated to the gate control addressing pulse/switching module 62 over a second RS485 bus line 118. Also, a third RS485 bus line 120 may be employed to communicate to and from other sub-system controllers 24 (see FIG. 2). The sub-system controllers 24 may monitor the third bus line 120 for a signal indicative of a faulty state. In addition, a fourth RS485 bus line 122 may be employed by the detector 22 to keep track of the independent addressable source being fired. As previously described, each of the sub-system controllers 24 is coupled to a respective data acquisition system 26 via a fourth communication link 32. In a presently contemplated embodiment, the third communication link 34 includes a high-voltage generator reset line 116, a Start/Controller Counts line 118, the third RS485 bus line 120, and high-voltage generator control lines RTL2 and RTL3, while the fourth RS485 bus line 122 may be configured to be the fourth communication link 32.

Figure 5:
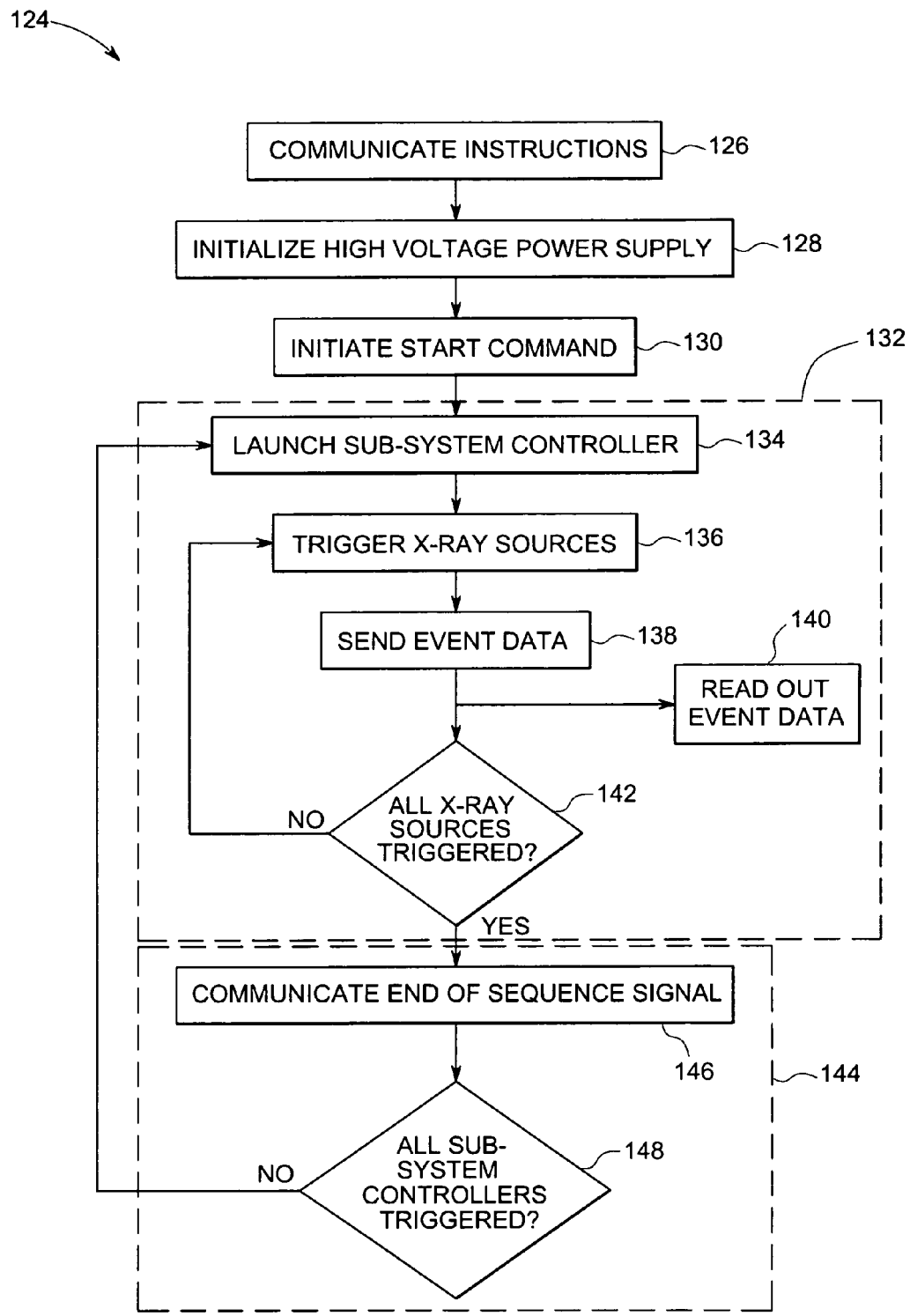
FIG. 5 is a flow chart illustrating an exemplary process of scanning a volume to be imaged, according to aspects of the present technique.

FIG. 5 is a flow chart of exemplary logic 124 for scanning a volume to be imaged. The method starts at step 126 where predetermined imaging sequence information is communicated from the system controller 18 (see FIG. 1) to the plurality of sub-system controllers (see FIG. 1) 24 via the first communication link 28. The predetermined imaging sequence information may include sequencing information and timing information required by the plurality of sub-systems 21 (see FIG. 1) to generate a desired view of an object to be imaged. In one embodiment, a user of the stationary CT system 10 (see FIG. 1) may select parameters indicative of a desired view of the object to be imaged. Accordingly, the system controller 18 communicates the desired imaging sequence to the plurality of sub-system controllers 24.

For example, the system controller 18 identifies a sub-system to be activated first in the desired imaging sequence. Subsequently, a firing position of the identified sub-system is communicated via the first communication link 28 to the corresponding sub-system controller. The desired imaging sequence is then communicated to the identified sub-system controller. Further, timing information related to the desired imaging sequence is also communicated to the identified sub-system controller. On completion of communicating desired imaging information to the identified sub-system controller, a signal indicative of a ready state is communicated from the identified sub-system controller to the system controller 18. The sequence of communicating firing position, desired imaging sequence and timing information is repeated until all the sub-system controllers 24 have been initiated. As previously noted, once each of the plurality of sub-system controllers have been handed off information necessary for executing the desired imaging sequence, each of the plurality of sub-system controllers communicates a signal indicative of a ready state to the system controller 18.

In addition, at step 126, operating commands from the system controller 18 to other sub-functions such as the high voltage generator 42, detectors 22, data acquisition systems 26 (see FIG. 1) and the gate drive power supply may be communicated. For example, operating and sequencing commands to be implemented by the system 10 are communicated to the data acquisition system electronics 26 and detector electronics 22 via the local Ethernet connection 104 (see FIG. 4). At step 128, the high voltage power supply 42 is initialized and set to a preset active threshold.

Once each of the plurality of sub-systems 21 has been loaded with the desired information, the system controller 18 communicates to an operator a ready state of the stationary CT system 10. The operator may then issue a command to the system controller 18 to initiate the firing (image data acquisition) sequence. Subsequent to receiving the command from the operator, the system controller 18 communicates a start synchronizing pulse to initiate the firing sequence of the sub-system controllers, at step 130. In one embodiment, the start synchronizing pulse may be a Start/Controller Counts command, which may be communicated to the sub-system controllers 24 via the second RS485 bus line 118.

At step 132 the firing sequence of the plurality of sub-system controllers 24 is initiated in accordance with the desired imaging sequence in response to the Start/Controller Counts command. The step of initiating the firing sequence 132 includes launching the sub-systems 21 in the predetermined order. Subsequently, at step 134, the Start/Controller Counts command pulse activates the first sub-system controller in the firing sequence. Also, the activated first sub-system controller takes control of the high voltage generator 42 (see FIG. 2). The activated sub-system controller then triggers the corresponding plurality of independent addressable X-ray sources to generate radiation data, at step 136. As each of the independent addressable X-ray sources is energized, a corresponding gate controller generates a count pulse. This count pulse is communicated to the corresponding data acquisition system 26 or corresponding detector 22 via the fourth RS485 bus line 122, at step 138. Subsequently, the radiation event data is read out by read out electronics from the data out module 36 (see FIG. 1) at step 140. Further, as indicated by step 142, steps 136, 138 and 140 are repeated until all the independent addressable X-ray sources corresponding to the activated sub-system controller called for in the particular imaging sequence have been triggered.

At step 144, the sub-system controllers 24 are cycled through in the predetermined order to execute the desired imaging sequence. At step 146, subsequent to completion of triggering of all the X-ray sources, the activated sub-system controller communicates an end of sequence signal to the system controller 18 and each of the other sub-system controllers. The Start/Controller Counts command line is activated. The subsequent sub-system controller in the firing sequence then uses this Start/Controller Counts command pulse to start a corresponding sequence of triggering X-ray sources, sending radiation event data and reading out the radiation event data. As previously noted, the radiation event data is communicated by sending out a Pulse/Counts command over the fourth RS485 bus line 122 each time an X-ray source is energized. This activated sub-system controller then transmits an end of sequence signal on completion of the triggering of the corresponding X-ray sources. Further, at step 148, steps 134-148 are repeated until all the sub-system controllers in the desired imaging sequence have been activated.

At the end of the overall sequence, the first sub-system controller releases the high voltage generator 42 thereby de-energizing the high voltage. In addition, as the sub-system controllers 24 complete their respective triggering sequences, a signal indicative of completion of the respective triggering sequences is communicated to the system controller 18 via the first communication link 28. Thus, the system controller 18 may be configured to monitor the sequencing progress through feedback from the system employing the first and second communication links 28, 30.

Steps 126-148 may be better understood with reference to FIG. 1. The system controller 18 communicates predetermined information to all the sub-system controllers 24 and other functional blocks. Further, the high voltage generator 42 is initialized. Subsequently, on receiving a signal indicative of a ready state of each of the plurality of sub-system controllers 24, the system controller 18 initiates the firing sequence. The plurality of sub-system controllers 24 may be then fired in the desired imaging sequence.

For example, in accordance with the desired imaging sequence, it may be desirable to trigger X-ray sources of the first sub-system. Accordingly, a first sub-system controller SSC-1 may be configured to trigger the first set of X-ray sources 20 in the first sub-system. A detector segment disposed diametrically opposite the first sub-system may be triggered by a corresponding data acquisition system to collect transmitted radiation. In other words, an eleventh data acquisition system DAS-11 may be configured to acquire the transmitted radiation data via the detector elements of the eleventh sub-system. Subsequently, the first sub-system controller SSC-1 may communicate an end of sequence signal to the system controller 18 and all other sub-system controllers in the imaging sequence via the second communication link 30.

The next sub-system in the firing sequence is then activated by the corresponding sub-system controller. For example, a sixth sub-system may follow the first sub-system in the desired imaging sequence. Subsequently, X-ray sources of a sixth sub-system may be triggered via a sixth sub-system controller SSC-6. The detector elements of the sub-system disposed diametrically opposite the sixth sub-system may be triggered to receive radiation data. Accordingly, the detector elements of the sixteenth sub-system may be triggered to receive radiation data at a sixteenth data acquisition system DAS-16.

The steps of initiating the radiation event via the sub-system controller and communicating the signal indicative of the end of sequence may be repeated until the desired imaging sequence is completed. Once the desired imaging sequence is completed, the first sub-system controller releases the high voltage generator 42. Further, as each of the sub-system controllers completes its firing sequence, a signal indicative of a completion status is communicated to the system controller 18 via the first communication link 28.

The various embodiments of stationary CT systems and methods described hereinabove facilitate a strategy to partition the stationary system in such a way so as to enable each sub-system to work independently while being synchronized with other sub-systems and functional blocks. A combination of the CAN interface and the RS485 interface is utilized to formulate a robust interconnection scheme for the stationary CT system. The CAN interface is employed to offload all sequencing and operational information from the system controller to the other functional blocks of the system, while the RS485 interface lines are employed to facilitate real-time communications and synchronizations. This robust interconnection and control scheme facilitates avoiding a large number of wires or conductors for interconnecting the system controller to the gate drive circuitry and the other functional blocks of the system. Further, besides dramatically reducing control wiring, improving timing and synchronization, the techniques described hereinabove facilitate a robust high noise immunity interconnection scheme that allows for a very fast firing field emitter stationary CT system with redundancy that employs high noise immunity twisted pair differential high bandwidth interfaces. Additionally, the interfaces used to communicate between the system controller and functional blocks are not sensitive to interconnection lengths. Furthermore, the localized controller provides a very high speed and precise timing controls of the field emitters.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A radiographic imaging system comprising:
a system controller;
a plurality of sub-system controllers, wherein each of the plurality of sub-system controllers is configured to facilitate generation of a radiation beam through an imaging volume in a desired sequence;
a first communication link configured to couple the system controller and each of the plurality of sub-system controllers, wherein the first communication link is configured to communicate sequencing commands and imaging protocol data;
a second communication link configured to couple the system controller and each of the plurality of sub-system controllers, wherein the second communication link is configured to communicate X-ray source event data, and wherein the X-ray source event data comprises a plurality of pulses of a plurality of individually addressable radiation sources; and
one or more detector sections configured to receive a transmitted radiation beam, wherein each of the one or more detector sections comprises at least one detector.

2. The system of claim 1, wherein the first communication link comprises a control-area-network bus and the second communication link comprises an RS485 bus.

3. The system of claim 1, wherein the second communication link communicates events in real-time.

4. The system of claim 1, further comprising a high voltage generator configured to provide a high voltage to the plurality of individually addressable radiation sources to facilitate generation of X-rays.

5. The system of claim 1, further comprising one or more data acquisition modules configured to acquire imaging data.

6. The system of claim 5, further comprising a third communication link configured to couple the system controller and the one or more data acquisition modules, wherein the third communication link is configured to communicate X-ray source event data to the one or more data acquisition modules and read out imaging data from the one or more data acquisition modules.

7. The system of claim 1, further comprising a fourth communication link configured to couple each of the sub-system controllers to a respective data acquisition module, wherein the fourth communication link is configured to communicate X-ray source event data to synchronize X-ray sources and detectors, and wherein the fourth communication link communicates events in real-time.

8. The system claim 1, further comprising a user interface, wherein the user interface is configured to set imaging parameters and acquisition parameters.

9. A radiographic imaging system comprising:
a system controller;
a plurality of sub-system controllers, wherein each of the plurality of sub-system controllers is configured to facilitate generation of a radiation beam through an imaging volume in a desired sequence;

a first communication link configured to couple the system controller and each of the plurality of sub-system controllers, wherein the first communication link is configured to communicate sequencing commands and imaging protocol data;

a second communication link configured to couple the system controller and each of the plurality of sub-system controllers, wherein the second communication link is configured to communicate X-ray source event data, and wherein the X-ray source event data comprises a plurality of pulses of individually addressable radiation sources;

one or more data acquisition modules;

a third communication link configured to couple the system controller and the one or more data acquisition modules, wherein the third communication link is configured to communicate X-ray source event data to the one or more data acquisition modules and read out imaging data from the one or more data acquisition modules;

a fourth communication link configured to couple each of the sub-system controllers to a respective data acquisition module, wherein the fourth communication link is configured to communicate X-ray source event data to synchronize X-ray sources and detectors; and one or more detectors sections configured to receive a transmitted radiation beam, wherein each of the one or more detector sections comprises at least one detector.

10. The system of claim 9, further comprising a high voltage generator configured to provide a high voltage to a plurality of X-ray sources to facilitate generation of X-rays.

11. The system claim 9, further comprising a user interface, wherein the user interface is configured to set imaging parameters and acquisition parameters.

12. A method for radiation imaging, the method comprising:

communicating predetermined imaging sequence information from a system controller to a plurality of sub-system controllers via a first communication link;

communicating a plurality of signals responsive to a ready state of the plurality of sub-system controllers to the system controller;

communicating an initiation command from the system controller to initiate each of the plurality of sub-system controllers; and communicating radiation source event data between each of the plurality of sub-system controllers via a second communication link in accordance with the predetermined imaging sequence;

generating radiation via a plurality of individually addressable radiation sources in response to the plurality of sub-system controllers;

acquiring a transmitted radiation beam via one or more detector sections;

obtaining data representative of the transmitted radiation beam acquired in accordance with the imaging sequence; and storing the data or an image generated from the data on a computer-readable medium, or displaying the data or the image on a display device, or a combination thereof.

13. The method of claim 12, wherein the predetermined imaging sequence information comprises sequencing information and timing information required by the plurality of sub-system controllers to generate a desired view of an object to be imaged.

14. The method of claim 12, wherein the step of communicating predetermined information comprises communicating sequencing information from the system controller to each of the plurality of sub-system controllers.

15. The method of claim 14, wherein the sequencing information comprises sequencing information related to each of the plurality of sub-systems between each of the plurality of sub-systems.

16. The method of claim 12, wherein the step of communicating radiation source event data comprises initiating a firing sequence of a plurality of distributed radiation sources.

17. The method of claim 12, further comprising communicating radiation source event data to a data acquisition module and reading out imaging data from a data acquisition module via a third communication link.

18. The method of claim 17, further comprising activating a respective detector to receive a transmitted beam responsive to an active state of a radiation source via a fourth communication link.

19. The method of claim 17, further comprising communicating radiation source event data between each of the plurality of sub-system controllers and the respective data acquisition systems via a fourth communication link.

20. The method of claim 12, wherein the step of initiating comprises:

providing an initializing signal to a first sub-system;

communicating a feedback signal from the first sub-system, where the feedback signal is indicative of completion of a firing activity; and providing the initializing signal to a subsequent sub-system.

21. The method of claim 20, further comprising monitoring progress of the firing activity via the second communication link.

22. The method of claim 12, wherein each of the one or more detector sections comprises at least one detector.

23. The method of claim 12, further comprising providing a high voltage to a plurality of radiation sources to facilitate generation of radiation.

24. The method of claim 12, further comprising acquiring imaging parameters and acquisition parameters via a user interface.

25. The method of claim 12, further comprising communicating an error signal indicative of a faulty sub-system to the system controller via the first communication link.

26. The method of claim 12, comprising displaying the data to a user via the display device.

27. The method of claim 12, wherein the radiation source event data comprises a plurality of pulses of a plurality of individually addressable radiation sources.

28. A method for radiation imaging, the method comprising:

communicating predetermined imaging sequence information from a system controller to a plurality of sub-system controllers via a first communication link;

communicating a plurality of signals responsive to a ready state of the plurality of sub-system controllers to the system controller;

communicating an initiation command from the system controller to initiate each of the plurality of sub-system controllers; and communicating radiation source event data between each of the plurality of sub-system controllers via a second communication link in accordance with the predetermined imaging sequence;

communicating radiation source event data to a data acquisition module and reading out imaging data from a data acquisition module via a third communication link;

activating a respective detector to receive a transmitted beam responsive to an active state of a radiation source via a fourth communication link generating radiation via a plurality of individually addressable radiation sources in response to the plurality of sub-system controllers;

acquiring a transmitted radiation beam via one or more detector sections;

obtaining data representative of the transmitted radiation beam acquired in accordance with the imaging sequence.

29. The method of claim 28, wherein the predetermined imaging sequence information comprises sequencing information and timing information required by the plurality of sub-system controllers to generate a desired view of an object to be imaged.

30. The method of claim 28, wherein the step of communicating predetermined information comprises communicating sequencing information from the system controller to each of the plurality of sub-system controllers.

31. The method of claim 30, wherein the sequencing information comprises sequencing information related to each of the plurality of sub-systems between each of the plurality of sub-systems.

32. The method of claim 28, wherein the step of communicating radiation source event data comprises initiating a firing sequence of a plurality of distributed radiation sources.

33. A method for radiation imaging, the method comprising:

communicating predetermined imaging sequence information from a system controller to a plurality of sub-system controllers via a first communication link;

communicating a plurality of signals responsive to a ready state of the plurality of sub-system controllers to the system controller;

communicating an initiation command from the system controller to initiate each of the plurality of sub-system controllers; and communicating radiation source event data between each of the plurality of sub-system controllers via a second communication link in accordance with the predetermined imaging sequence;

providing a high voltage to a plurality of individually addressable radiation sources to facilitate generation of radiation;

generating radiation via the plurality of individually addressable radiation sources in response to the plurality of sub-system controllers;

acquiring a transmitted radiation beam via one or more detector sections; and obtaining data representative of the transmitted radiation beam acquired in accordance with the imaging sequence.

34. The method of claim 33, wherein the radiation source event data comprises a plurality of pulses of a plurality of individually addressable radiation sources.

35. The method of claim 33, wherein the step of initiating comprises:

providing an initializing signal to a first sub-system;

communicating a feedback signal from the first sub-system, where the feedback signal is indicative of completion of a firing activity; and providing the initializing signal to a subsequent sub-system.

36. The method of claim 35, further comprising monitoring progress of the firing activity via the second communication link.

* * * * *